United States Patent [19]

Remy et al.

[11] 4,412,999
[45] Nov. 1, 1983

[54] ANTI-EMETIC ESTERS OF CYPROHEPTADINE-3-CARBOXYLIC ACID AND STRUCTURALLY RELATED COMPOUNDS

[75] Inventors: David C. Remy, North Wales; Bradley V. Clineschmidt, Norristown, both of Pa.

[73] Assignee: Merck & Co., Inc., Rahway, N.J.

[21] Appl. No.: 368,257

[22] Filed: Apr. 14, 1982

[51] Int. Cl.$^3$ .................. A61K 31/445; C07D 401/12
[52] U.S. Cl. .................................... 424/267; 546/196; 546/199; 546/202; 546/203
[58] Field of Search ................ 546/203, 199; 424/267

[56] References Cited

U.S. PATENT DOCUMENTS

| 3,014,911 | 12/1961 | Engelhardt | 546/203 |
| 3,981,877 | 9/1976 | Prugh | 424/267 X |
| 4,066,772 | 1/1978 | Vandenberk | 424/267 |
| 4,072,756 | 2/1978 | Ebnother et al. | 424/267 |
| 4,076,714 | 2/1978 | Anderson et al. | 424/267 |
| 4,086,350 | 4/1978 | Zirkle | 424/267 |
| 4,160,031 | 7/1979 | Remy | 424/267 |

FOREIGN PATENT DOCUMENTS 1084996 9/1967 United Kingdom ................ 546/203

OTHER PUBLICATIONS

March, J., *Advanced Organic Chemistry*, McGraw Hill, New York, 1968, p. 323.
*Postgraduate Medical Journal*, 55, (1979), Supplement (1), Hoffrand, B., (editor), pp. 3—4.

*Primary Examiner*—Richard A. Schwartz
*Attorney, Agent, or Firm*—William H. Nicholson; Mario A. Monaco

[57] ABSTRACT

Certain esters of cyproheptadine-3-carboxylic acid and its bioisosteres are peripherally selective dopamine antagonists useful in the treatment of emesis caused by stimulation of dopamine receptors of the chemoreceptor trigger zone, as well as emesis and nausea resulting from other causes including post operative emesis, chronic pediatric vomiting, radiotherapy and chemotherapy induced emesis, and nausea associated with migrane attacks and dysmenorrhea or arising idiopathically.

They are also useful in the treatment of gastrointestinal disorders, such as gastro-oesophageal reflux caused by stimulation of dopamine receptors in the stomach or other causes and dyspepsia arising from delayed gastric emptying, post prandial dyspepsia or dyspepsia of unknown etiology.

20 Claims, No Drawings

ANTI-EMETIC ESTERS OF CYPROHEPTADINE-3-CARBOXYLIC ACID AND STRUCTURALLY RELATED COMPOUNDS

BACKGROUND OF THE INVENTION

This invention is concerned with compounds of structural formula I:

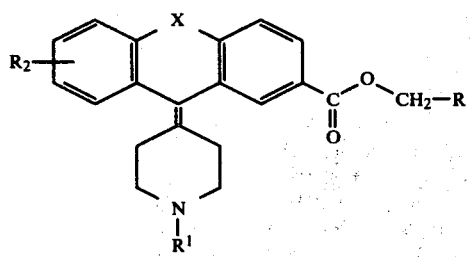

wherein X is —CH=CH—, —CH$_2$—CH$_2$—, —CH$_2$—O—, —O—CH$_2$—, —S—CH$_2$—, —CH$_2$—S—, —S— or —O—, and R is a 5- or 6-membered nitrogen heterocyclic ring optionally fused to a benzo group, which are antiemetic agents because of their peripheral dopamine antagonist activity.

Severe emesis, and gastro-oesophageal reflux and/or dyspepsia caused by stimulation of peripheral dopamine receptors, are responsive to treatment with dopamine antagonists such as antipsychotic agents. However, such treatment may be accompanied by rather pronounced undesirable central nervous system effects. Furthermore, in the treatment of parkinsonism with a dopaminergic agent, such as bromocriptine or 1-dopa, the severe emetic and other side effects thereof cannot be treated successfully with a centrally active dopamine antagonist without also blocking the desired antiparkinsonian action. Thus, there was a need for a drug which would control side effects of that origin but would not have the undesirable central effects of known dopamine antagonists nor interefere with the central dopamine agonist activity of a dopaminergic agent. One such agent, domperidone, has been described in British Pat. No. 1,542,514.

Now, with the present invention there is provided a group of novel compounds which have been derived from powerful dopamine antagonists in a manner that limits or eliminates their ability to traverse the blood-brain barrier and are thereby peripherally selective dopamine antagonists and are useful for the treatment of emesis caused by stimulation of dopamine receptors of the chemoreceptor trigger zone, as well as emesis and nausea resulting from other causes including post operative emesis, chronic pediatric vomiting, radiotherapy and chemotherapy induced emesis, and nausea associated with migraine attacks and dysmenorrhea or arising idiopathically.

They are also useful in the treatment of gastrointestinal disorders, such as gastro-oesophageal reflux caused by stimulation of dopamine receptors in the stomach or other causes and dyspepsia arising from delayed gastric emptying, post prandial dyspepsia or dyspepsia of unknown etiology.

There are also provided novel processes for the preparation of the novel compounds; pharmaceutical formulations employing one of the novel compounds as the active agent alone or in combination with a dopamine agonist; and a method of treating emesis, gastro-oesophageal reflux and/or dyspepsia by the administration of an effective dopamine antagonistic amount of a novel compound of this invention.

DETAILED DESCRIPTION OF THE INVENTION

The novel compounds of this invention have structural formula I:

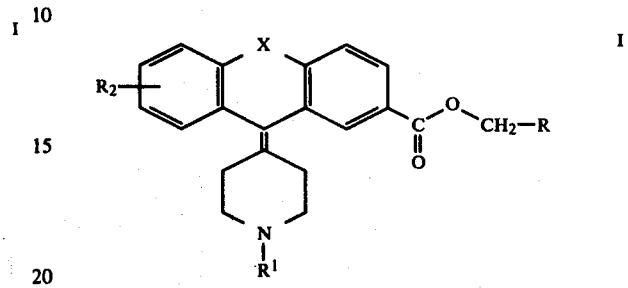

or a pharmaceutically acceptable salt thereof, wherein X is (1) —CH=CH—, (2) —CH$_2$—CH$_2$—, (3) —CH$_2$—O—, (4) —O—CH$_2$—, (5) —CH$_2$—S—, (6) —S—CH$_2$—, (7) —S—, or (8) —O—;

R is

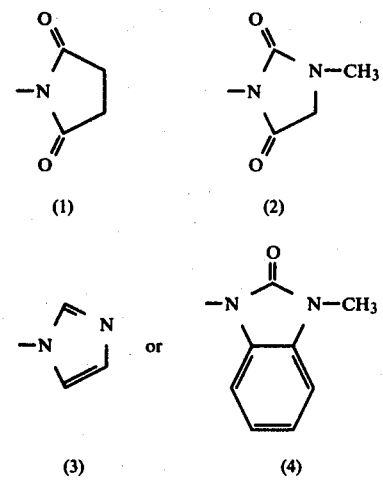

R$^1$ is (1) C$_{1-3}$ alkyl, or

(2)

and
R$^2$ is (1) hydrogen, (2) C$_{1-3}$ alkyl, or (3) fluoro.

In a preferred embodiment of the novel compounds of this invention X is —CH=CH—, —CH$_2$—CH$_2$—, or —S—; R is

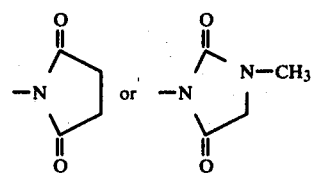

R$^1$ is —CH$_3$; and R$^2$ is hydrogen.

In an even more preferred embodiment X is —CH=CH—; R is

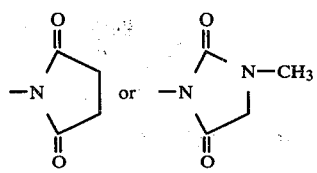

R[1] is —CH$_3$ and R[2] is hydrogen.

The group of novel compounds wherein X is —CH=CH— exist as dextrorotatory and levorotatory atropisomers and racemic mixtures thereof. Substantially all of the desired peripheral dopamine antagonist activity is provided by the levorotatory enantiomers and accordingly, although the racemates are included within the scope of the novel peripherally active dopamine antagonist compounds of this invention, the levorotatory enantiomers are a preferred embodiment thereof.

The pharmaceutically acceptable salts of the novel compounds of this invention are acid addition salts formed from a novel compound and an organic or inorganic acid recognized by the art as providing a pharmaceutically acceptable acid addition salt, such as hydrochloride, hydrobromide, dihydrogen phosphate, sulfate, citrate, pamoate, pyruvate, napsylate, isethionate, maleate, fumarate, or the like.

These salts are readily prepared by mixing solutions of equimolecular amounts of the free base compound and the desired acid in suitable solvents such as water, alcohols, ether or chloroform, followed by recovery of the product by collecting the precipitated salt or evaporation of the solvent.

The novel process of this invention is illustrated by the following reaction scheme:

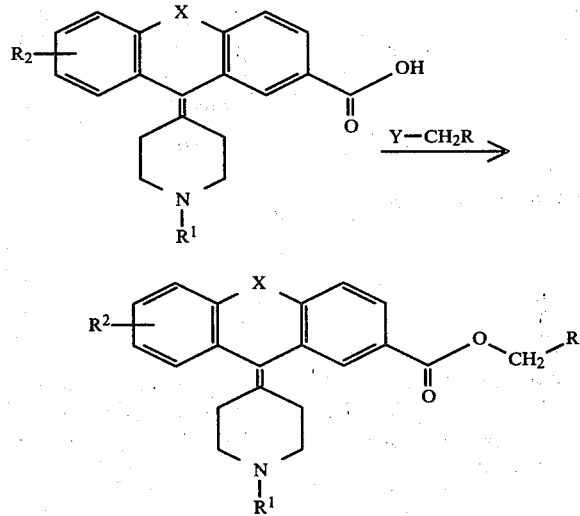

wherein X, R, R[1], and R[2] have the meanings previously assigned and Y is halogen, selected from Cl, Br, or I. It comprises mixing the two reactants in an organic solvent which is inert to the conditions of the reaction, such as hexamethyl phosphoramide (HMPA), dimethyl sulfoxide (DMSO), dimethylformamide (DMF), 1,1,3,3-tetramethylurea, or the like, in the presence of an acid acceptor such as a strong organic base, for example, triethylamine (TEA), N-methylpiperidine, pyridine or the like, an inorganic base such as sodium carbonate, aqueous sodium hydroxide or the like, or a strongly basic ion exchange resin such as Dowex-1(OH$^-$), IRA-400(OH$^-$), or the like. The preferred solvents are HMPA and DMSO and the preferred acid acceptor is TEA. The condensation reaction is conveniently run at ambient temperatures (15°–25° C.) although any temperature from about 5° C. to about 100° C. is reasonable. Depending partially on temperature, the reaction is substantially complete in about 6 to about 24 hours. It is convenient to let it go overnight, or for about 16 to about 20 hours.

The enantiomers of the cyproheptadine ester derivatives are prepared in accordance with the above described process from the enantiomers of the cyproheptadine-3-carboxylic acids or, if desired, the racemates of the desired esters are resolved by known techniques such as through preferential crystallization of a diastereomeric salt such as that formed with di-p-toluyl-d-tartaric acid, as exemplified by the resolution of the simple ethyl ester in Example 1, step B.

In view of their useful activities, the compounds of Formula (I) may be formulated into various pharmaceutical compositions for administration purposes. To prepare the pharmaceutical compositions of this invention, an effective dopamine antagonist amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, preferably, for administration orally, rectally or by parenteral injection. For example, in preparing the compositions in oral dosage form, any of the usual pharmaceutical media may be employed, such as, water, glycols, oils and alcohols for oral liquid preparations such as suspensions syrups, elixirs and solutions; or solid carriers such as starches, sugars, kaolin, lubricants, binders, and disintegrating agents for powders, pills, capsules and tablets. Because of their ease in administration, tablets and capsules are the most advantageous oral dosage unit form, for which solid pharmaceutical carriers are obviously employed. For parenteral compositions, the carrier will usually comprise sterile water, at least in large part, though other ingredients, for example, may be prepared in which the carrier comprises saline solution, glucose solution or a mixture of saline and glucose solution. Injectable suspensions may also be prepared for which appropriate liquid carriers and suspending agents may be employed. Acid addition salts of (I), due to their increased water solubility compared to the corresponding base form, are obviously more suitable in the preparation of aqueous compositions.

It is especially advantageous to formulate the aforementioned pharmaceutical compositions in dosage unit form for ease of administration and uniformity of dosage. By the term "dosage unit form" as used herein is meant physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonsful and tablespoonsful, and segregated multiples thereof.

The compounds of Formula I are advantageously formulated in combination with a dopamine agonist such as used in the treatment of parkinsonism.

The amount of active ingredient of Formula I in a unit dosage may be from 1 to 400 mg and preferably from 5 to 250 mg whether used alone or in combination with a dopamine agonist.

The novel method of treatment of this invention comprises the administration of one of the novel compounds, prophylactically or therapeutically to a patient in need of a peripherally selective dopamine antagonist. The route of administration can be oral, rectal, intravenous, intramuscular, or subcutaneous. Doses of 0.1 to 20 mg/kg/day and preferably of 0.5 to 10 mg/kg/day of active ingredient are generally adequate, and if preferred it can be administered in divided doses given two to four times daily.

It is to be noted that the precise unit dosage form and dosage level depend upon the requirements of the individual being treated and, consequently, are left to the discretion of the therapist.

In the previous description of the novel compounds it was pointed out that the cyproheptadine derivatives (X=—CH=CH—) exist as enantiomers and that the dextrorotatory enantiomers are substantially devoid of antiemetic activity. Nonetheless those dextrorotatory enantiomers form another embodiment of this invention being useful as starting materials for the racemic products resulting from a racemization process. The racemization process comprises heating a solution of the dextro enantiomer in an inert solvent such as toluene, xylene, chlorobenzene, or the like until optical activity disappears. Temperatures of 65° to about 150° C. for about 10 to 30 hours may be employed, and refluxing toluene for about 26 hours is preferred.

EXAMPLE 1

(−)-(2,5-Dioxo-1-Pyrrolidinyl)methyl 5-(1-methyl-4-piperidinylidene)-5H-dibenzo[a,d]cycloheptene-3-carboxylate Step A: Preparation of (±)-ethyl 5-(1-methyl-4-piperidylidene)-5H-dibenzo[a,d]cycloheptene-3-carboxylate Racemic 5-(1-methyl-4-piperidylidene)-5H-dibenzo[a,d]cycloheptene-3-carboxylic acid (0.03 mole) and an equal molar amount of boron trifluoride etherate in 60 ml of absolute ethanol was refluxed overnight. The solution was evaporated to dryness and the residue was partitioned between ether and a saturated aqueous solution of sodium bicarbonate. The ether was separated and dried over MgSO₄. The resulting ethyl ester, crystallized from acetonitrile, had m.p. 102°–103° C.

Step B: Resolution of (±)-ethyl 5-(1-methyl-4-piperidylidene)-5H-dibenzo[a,d]cycloheptene-3-carboxylate To a solution of 5.00 g (0.0139 mole) of the racemate in 50 ml of absolute ethanol was added 5.38 g (0.0139 mole) of di-p-toluoyl-d-tartaric acid in 50 ml of ethanol. The homogeneous solution was warmed and then allowed to cool. The crystalline precipitate that formed on cooling was removed by filtration, washed with cold ethanol, and dried at 65° to give 3.90 g of material, designated A. The clear ethanol filtrate and washings were combined and designated B.

The 3.90 g of A was recrystallized twice from absolute ethanol to give a product with constant rotation, $[\alpha]_{589}^{25} -165°$, $[\alpha]_{578}^{25} -176°$, $[\alpha]_{546}^{25} -211°$, $[\alpha]_{436}^{25} -523°$, (c=0.0074 g/ml pyridine). This material (3.46 g) was dissolved in water and a solution of sodium carbonate was added. The resulting precipitate was extracted into ether, washed with water, and dried over magnesium sulfate. After filtering, the ether was evaporated. The residue was triturated with acetonitrile, collected by filtration and dried at 78° in vacuo to give 1.50 g of (−)-ethyl 5-(1-methyl-4-piperidylidene)-5H-dibenzo[a,d]cycloheptene-3-carboxylate, m.p. 94°–96°; $[\alpha]_{589}^{25} -207°$, $[\alpha]_{578}^{25} -220°$, $[\alpha]_{546}^{25} -268°$, $[\alpha]_{436}^{25} -728°$, (c=0.008895 g/ml CHCl₃).

The ethanol filtrate and washings, B, were allowed to stand at room temperature for six days during which time the supernatant liquid was decanted from a small amount of crystalline residue. This supernatent liquid was allowed to stand fourteen days at room temperature, after which time it was decanted again. The ethanol was removed by evaporation. The residue was dissolved in water and treated with an excess of a solution of sodium carbonate. The resulting precipitate was extracted into ether, washed with water, and dried over magnesium sulfate. After filtering, the ether was evaporated to give 2.03 g of (+)-ethyl 5-(1-methyl-4-piperidylidene)-5H-dibenzo[a,d]cycloheptene-3-carboxylate, m.p. 94°–95°. This material was 93% optically pure as determined by its rotation; $[\alpha]_{589}^{25} +178°$, $[\alpha]_{578}^{25} +189°$; $[\alpha]_{546}^{25} +230°$, $[\alpha]_{436}^{25} +622°$ (c=0.00869 g/ml CHCl₃).

Step C: Preparation of (−)-5-(1-methyl-4-piperidylidene)-5H-dibenzo[a,d]cycloheptene-3-carboxylic acid A solution of 1.24 g of (−)-ethyl 5-(1-methyl-4-piperidylidene)-5H-dibenzo[a,d]cycloheptene-3-carboxylate and 4.12 ml of 2 N potassium hydroxide in 55 ml of methanol was stirred at room temperature for seven days. The methanol was removed by evaporation at 25°. The residue was dissolved in water and extracted with 50 ml of ether. The clear, colorless aqueous phase was acidified with glacial acetic acid. The white precipitate that formed was removed by filtration, and washed thoroughly with water. After drying at 100° in vacuo, 1.08 g of (−)-5-(1-methyl-4-piperidylidene)-5H-dibenzo[a,d]cycloheptene-3-carboxylic acid was obtained, m.p. 300°–305°; $[\alpha]_{589}^{25} -180°$; $[\alpha]_{578}^{25} -194°$; $[\alpha]_{546}^{25} -239°$; $[\alpha]_{436}^{25} -675°$; (c=0.004968 g/ml 0.10 NHCl). R_f: 0.70 (fluorescent silica gel, n-butanol/acetic acid/water (5:2:3).

Similarly, there was prepared 93% optically pure (+)-5-(1-methyl-4-piperidylidene)-5H-dibenzo[a,d]cycloheptene-3-carboxylic acid, m.p. 302°–305°, $[\alpha]_{589}^{25} +152°$; $[\alpha]_{578}^{25} +163°$; $[\alpha]_{546}^{25} +201°$; $[\alpha]_{436}^{25} +572°$; (c=0.005611 g/ml 0.10 NHCl).

Step D: Preparation of (−)-(2,5-Dioxo-1-Pyrrolidinyl) methyl 5-(1-methyl-4-piperidinylidene)-5H-dibenzo[a,d]cycloheptene-3-carboxylate To a mixture of 2.00 g (0.00544 mole) of (−)-5-(1-methyl-4-piperidylidene-5H-dibenzo[a,d]-cyclohepten-5-ylidene)-3-carboxylic acid, 10 ml of dimethylsulfoxide and 0.55 g (0.00544 mole) of triethylamine was added a solution of 1.05 g (0.00544 mole) of succinimidomethyl bromide in 10 ml of dimethyl sulfoxide. The mixture was stirred overnight at ambient temperature. The mixture was filtered to recover unreacted starting acid. The recovered acid, 0.55 g of triethylamine, 1.05 g of succinimidomethyl bromide, and 12 ml of hexamethylphosphoramide were mixed and heated on a steam bath for 5 minutes. The homogeneous solution was allowed to stir at ambient temperature overnight. The dimethyl sulfoxide filtrate obtained above was combined with the hexamethylphosphoramide solution and this mixture was poured into 400 ml of water containing 50 ml of an aqueous, saturated sodium carbonate solution. The mixture was extracted with three 100 ml portions of toluene, and the combined toluene extracts were washed with water, dried over magnesium sulfate, filtered, and the solvent was removed by evaporation. Recrystallization of the residue from acetonitrile afforded pure (−)-(2,5-dioxo-1-pyrrolidinyl)methyl 5-(1-methyl-4-piperidinylidene)-5H-dibenzo[a,d]cycloheptene-3-carboxylate, m.p. 186°–188° C.; $[\alpha]_{589}^{25} -211°$; $[\alpha]_{578}^{25} -255°$; $[\alpha]_{546}^{25} -274°$; $[\alpha]_{436}^{25} -752°$; (c=0.5141, CHCl$_3$).

Anal. Calcd. for $C_{27}H_{26}N_2O_4$: C, 73.29; H, 5.92; N, 6.33. Found: C, 73.09; H, 5.96; N, 6.37.

Employing the procedure substantially as described in Example 1, Step D, the following were prepared from succinimidomethyl bromide and the appropriate carboxylic acid:

(±)-(2,5-Dioxo-1-Pyrrolidinyl)methyl 5-(1-methyl-4-piperidinylidene)-5H-dibenzo[a,d]cycloheptene-3-carboxylate m.p. 162°–165° C.

(+)-(2,5-Dioxo-1-Pyrrolidinyl)methyl 5-(1-methyl-4-piperidinylidene)-5H-dibenzo[a,d]cycloheptene-3-carboxylate m.p. 185°–187° C.

(2,5-Dioxo-1-pyrrolidinyl)methyl 10,11-dihydro-5-(1-methyl-4-piperidinylidene)-5H-dibenzo[a,d]cycloheptene-3-carboxylate, m.p. 140°–142° C. and (2,5-Dioxo-1-Pyrrolidinyl)methyl 9-(1-methyl-4-piperidinylidene)-9H-thioxanthene-2-carboxylate, m.p. 178°–180° C.

EXAMPLE 2

(±)-(3-Methyl-2,5-dioxo-1-imidazolidinyl)methyl 5-(1-methyl-4-piperidinylidene)-5H-dibenzo[a,d]cycloheptene-3-carboxylate To a mixture of 1.0 g (0.00302 mole) of (±)-5-(1-methyl-4-piperidylidene)-5H-dibenzo[a,d]cycloheptene-3-carboxylic acid, 0.31 g (0.0030 mole) of triethylamine and 4 ml of hexamethylphosphoramide was added 0.456 g (0.0030 mol) of 1H-1-chloromethyl-3-methyl-2,5-dioxo-2,3,4,5-tetrahydroimidazole. The mixture was stirred and heated in an oil bath at 100° C. for 18 hours. After cooling, 25 ml of water and 25 ml of a saturated solution of sodium carbonate were added to the reaction. The mixture then was extracted with ten 50 ml aliquots of ether. The combined ether extracts were washed with ten 75 ml portions of water, dried over magnesium sulfate, filtered, and the solvent was removed on a rotary evaporator. The white crystalline residue was recrystallized from acetonitrile to afford (±)-(3-methyl-2,5-dioxo-1-imidazolidinyl)methyl 5-(1-methyl-4-piperidinylidene)-5H-dibenzo[a,d]cycloheptene-3-carboxylate, m.p. 192°–194°.

Anal. Calcd. for $C_{27}H_{27}N_3O_4$: C, 70.88; H, 5.95; N, 9.19. Found: C, 70.60; H, 6.12; N, 9.20.

EXAMPLE 3

(−)-(3-Methyl-2,5-dioxo-1-imidazolidinyl)methyl 5-(1-methyl-4-piperidinylidene)-5H-dibenzo[a,d]cycloheptene-3-carboxylate When the levorotatory enantiomer was substituted for the racemic carboxylic acid in the procedure of Example 2, and the reaction mixture was heated on the steam bath for 10 minutes and then was kept at room temperature for 18 hours there was obtained (−)-(3-methyl-2,5-dioxo-1-imidazolidinyl)methyl 5-(1-methyl-4-piperidinylidene)-5H-dibenzo[a,d]cycloheptene-3-carboxylate, m.p. 188°–189° C.; $[\alpha]_{589} -207$; $[\alpha]_{578} -220°$; $[\alpha]_{546} -270°$; $[\alpha]_{436} -733°$ (CHCl$_3$).

Anal. Calcd. for $C_{27}H_{27}N_3O_4$: C, 70.88; H, 5.95; N, 9.19. Found: C, 71.02; H, 6.05; N, 9.29.

EXAMPLE 4

(+)-(3-Methyl-2,5-dioxo-1-imidazolidinyl)methyl 5-(1-methyl-4-piperidinylidene)-5H-dibenzo[a,d]cycloheptene-3-carboxylate When the dextrorotatory enantiomer was substituted for the racemic carboxylic acid in the procedure of Example 2, and the reaction mixture was heated on the steam bath for 10 minutes and then was kept at room temperature for 24 hours, there was obtained (+)-(3-methyl-2,5-dioxo-1-imidazoli dinyl)methyl 5-(1-methyl-4-piperidinylidene)-5H-dibenzo[a,d]cycloheptene-3-carboxylate, m.p. 189°–190°; $[\alpha]_{589}^{25} +208°$; $[\alpha]_{578}^{25} +222°$; $[\alpha]_{546}^{25} +270°$; $[\alpha]_{436}^{25} +733°$ (CHCl$_3$).

Anal. Calcd. for $C_{27}H_{27}N_3O_4$: C, 70.88; H, 5.95; N, 9.19. Found: C, 71.12; H, 6.10; N, 9.20.

EXAMPLE 5

Racemization of (+)-(3-methyl-2,5-dioxo-1-imidazolidinyl)methyl 5-(1-methyl-4-piperidinylidene)-5H-dibenzo[a,d]cycloheptene-3-carboxylate A solution of 0.50 g of (+)-(3-methyl-2,5-dioxo-1-imidazolidinyl)methyl 5-(1-methyl-4-piperidinylidene)-5H-dibenzo[a,d]cycloheptene-3-carboxylate, $[\alpha]_{589}^{25} = +208°$, in 50 ml of toluene was stirred and refluxed for 26 hours. At the end of this time, the solution showed $[\alpha]_{589}^{25} = 0.0°$. Evaporation of the toluene in vacuo gave chromatographically pure (+)-(3-methyl-2,5-dioxo-1-imidazolidinyl)methyl 5-(1-methyl-4-piperidinylidene)-5H-dibenzo[a,d]cycloheptene-3-carboxylate, m.p. 191°–194°.

EXAMPLE 6

(±)-((2,3-Dihydro-3-methyl-2-oxo-1H-Benzimidazol-1-yl)-methyl) 5-(1-methyl-4-piperidinylidene)-5H-dibenzo-[a,d])cycloheptene-3-carboxylate To a mixture of 1.00 g (0.00302 mol) of (±)-5-(1-methyl-4-piperidylidene)-5H-dibenzo[a,d]-cycloheptene-3-carboxylic acid, 0.31 g (0.0030 mol) of triethylamine, and 8 ml of hexamethylphosphoramide (HMPA) was added 0.60 g (0.0031 mol) of 1-chloromethyl-1,2-dihydro-3-methyl-3H-benzimidazol-2-one. The mixture was stirred and heated in an oil bath at 100° C. for 10 hours. After cooling, 50 ml of a saturated solution of sodium carbonate and 200 ml of water was added to the reaction. The mixture was extracted with four 75 ml aliquots of toluene. The combined toluene extracts were washed with five 100 ml portions of water, dried over magnesium sulfate, filtered, and the toluene was removed on a rotary evaporator. The white crystalline residue was recrystallized from acetonitrile to afford 0.64 g (43%) of (±)-(2,3-dihydro-3-methyl-2-oxo-1H-benzimidazol-1-yl)-methyl) 5-(1-methyl-4-piperidinylidene)-5H-dibenzo-[a,d])cycloheptene-3-carboxylate, m.p. 182°–184° C.

Anal. Calcd. for $C_{31}H_{29}N_3O_3$: C, 75.74; H, 5.95; N, 8.55. Found: C, 75.75; H, 6.01; N, 8.66.

EXAMPLE 7

(±)-(1H-Imidazol-1-yl)methyl 5-(1-methyl-4-piperidylidene)-5H-dibenzo[a,d]-cycloheptene-3-carboxylate Employing the procedure substantially as described in Example 3 but substituting for the 1-chloromethyl-1,3-dihydro-3-methyl-3H-benzimidazole-2-one used therein, an equimolar amount of (1H-imidazol-1-yl)methyl bromide, the racemic subject compound was prepared, in comparable yield, m.p. 118°–121° C.

Anal. Calcd. for $C_{26}H_{25}N_3O_2$: C, 75.89; H, 6.12; N, 10.21. Found: C, 75.51; H, 6.17; N, 10.18.

Following the procedures substantially as described in Examples 1 through 7, the following compounds are prepared from the appropriate carboxylic acid and $RCH_2Br$ in the presence of TEA.

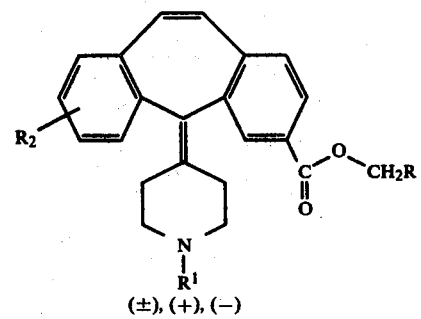

| R | $R^1$ | $R^2$ | optical activity |
|---|---|---|---|
| (benzimidazolone) | —CH₃ | H | (−) |
| | —CH₃ | H | (+) |
| | —CH₃ | 7-CH₃ | (±), (+), (−) |
| | —CH₃ | 7-F | (±), (+), (−) |
| | —CH₂C₃H₅ | H | (±), (+), (−) |
| | —CH₂C₃H₅ | 7-CH₃ | (±), (+), (−) |
| | —CH₂C₃H₅ | 7-F | (±), (+), (−) |

(±), (+), (−)

| R | $R^1$ | $R^2$ | optical activity |
|---|---|---|---|
| (succinimide) | —CH₃ | 7-CH₃ | (±), (+), (−) |
| | —CH₃ | 7-F | (±), (+), (−) |
| | —CH₂C₃H₅ | H | (±), (+), (−) |
| | —CH₂C₃H₅ | 7-CH₃ | (±), (+), (−) |
| | —CH₂C₃H₅ | 7-F | (±), (+), (−) |
| (methylimidazolidinedione) | —CH₃ | 7-CH₃ | (±), (+), (−) |
| | —CH₃ | 7-F | (±), (+), (−) |
| | —CH₂C₃H₅ | H | (±), (+), (−) |
| | —CH₂C₃H₅ | 7-CH₃ | (±), (+), (−) |
| | —CH₂C₃H₅ | 7-F | (±), (+), (−) |
| (imidazole) | —CH₃ | H | (+), (−) |
| | —CH₃ | 7-CH₃ | (±), (+), (−) |
| | —CH₃ | 7-F | (±), (+), (−) |
| | —CH₂C₃H₅ | H | (±), (+), (−) |
| | —CH₂C₃H₅ | 7-CH₃ | (±), (+), (−) |
| | —CH₂C₃H₅ | 7-F | (±), (+), (−) |

X = —CH₂CH₂—, —CH₂—O—, —O—CH₂—, —CH₂—S—, —S—CH₂—, —S— or —O—

| R | $R^1$ | $R^2$ |
|---|---|---|
| (succinimide) | —CH₃ | 7-CH₃ |
| | —CH₃ | 7-F |
| | —CH₂C₃H₅ | H |
| | —CH₂C₃H₅ | 7-CH₃ |
| | —CH₂C₃H₅ | 7-F |
| (methylimidazolidinedione) | —CH₃ | H |
| | —CH₃ | 7-CH₃ |
| | —CH₃ | 7-F |
| | —CH₂C₃H₅ | H |
| | —CH₂C₃H₅ | 7-CH₃ |
| | —CH₂C₃H₅ | 7-F |
| (imidazole) | —CH₃ | H |
| | —CH₃ | 7-CH₃ |
| | —CH₃ | 7-F |
| | —CH₂C₃H₅ | H |
| | —CH₂C₃H₅ | 7-CH₃ |
| | —CH₂C₃H₅ | 7-F |

-continued

X = —CH₂CH₂—, —CH₂—O—, —O—CH₂—, —CH₂—S—, —S—CH₂—, —S— or —O—

| R | R¹ | R² |
|---|---|---|
| (N-acetyl-N'-methylbenzimidazolone group) | —CH₃ | H |
| | —CH₃ | 7-CH₃ |
| | —CH₃ | 7-F |
| | —CH₂C₃H₅ | H |
| | —CH₂C₃H₅ | 7-CH₃ |
| | —CH₂C₃H₅ | 7-F |

What is claimed is:

1. A compound of structural formula:

(Structure I: substituted xanthene/thioxanthene-type with R₂, X bridge, piperidylidene N-R¹, and —C(O)—O—CH₂—R ester)

or a pharmaceutically acceptable salt thereof, wherein
X is (1) —CH=CH—, or (2) —CH₂—CH₂—;
R is (1) succinimide
(2) N-methyl-hydantoin-like ring
(3) imidazole
(4) N-methyl-benzimidazolone R¹ is (1) C₁₋₃alkyl, or (2)

—CH₂—◁ (cyclopropylmethyl);

and

R² is (1) hydrogen, (2) C₁₋₃alkyl, or (3) fluoro.

2. The compound of claim 1 wherein X is —CH=CH—, or —CH₂—CH₂—; R is (1) succinimide or (2) N-methyl-hydantoin R¹ is —CH₃ and R² is hydrogen.

3. The compound of claim 2 wherein X is —CH=CH—; R is (1) succinimide or (2) N-methyl-hydantoin R¹ is —CH₃ and R² is hydrogen.

4. The compound of claim 3, wherein R is (N-methyl-hydantoin group)

5. The compound of claim 1, 2 or 3 wherein X is —CH=CH— which is a racemate, a (+)-enantiomer or a (−)-enantiomer.

6. A pharmaceutical peripherally selective dopamine antagonist composition comprising a pharmaceutical carrier and an effective peripherally selective dopamine antagonist amount of a compound of structural formula:

(Structure I repeated)

or a pharmaceutically acceptable salt thereof, wherein
X is (1) —CH=CH—, or (2) —CH₂—CH₂—;
R is (1) succinimide (2) N-methyl-hydantoin -continued

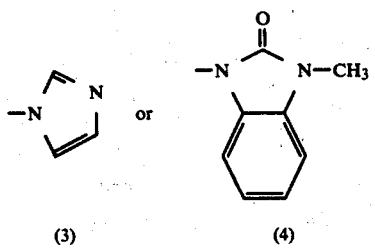

(3)     (4)

R¹ is (1) C₁₋₃alkyl, or (2)

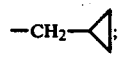

and

R² is (1) hydrogen, (2) C₁₋₃alkyl, or (3) fluoro.

7. The composition of claim 6 comprising the compound wherein X is —CH=CH—, or —CH₂—CH₂;

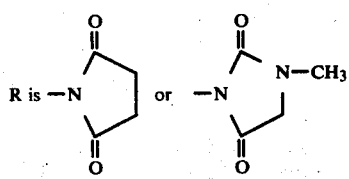

R¹ is —CH₃ and R² is hydrogen.

8. The composition of claim 7 comprising the compound wherein X is —CH=CH—; R is

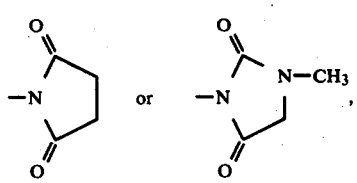

R¹ is —CH₃ and R² is hydrogen.

9. The composition of claim 8, wherein R is

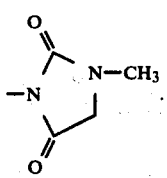

10. The composition of claim 6, 7 or 8 wherein X is —CH=CH— and Compound I is a racemate or a (—)-enantiomer.

11. A pharmaceutical centrally selective dopamine agonist composition comprising a pharmaceutical carrier, a dopamine agonist and an effective peripherally selective dopamine antagonist amount of a compound of structural formula:

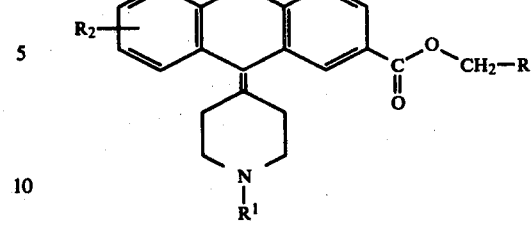

or a pharmaceutically acceptable salt thereof, wherein X is (1) —CH=CH—, or (2) —CH₂—CH₂—;

R is

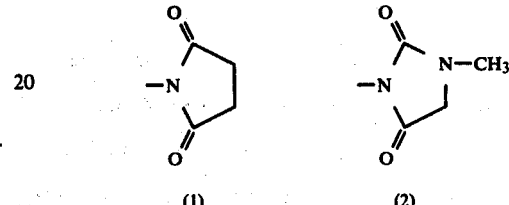

(1)     (2)

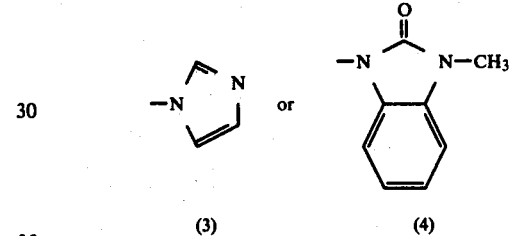

(3)     (4)

R¹ is (1) C₁₋₃alkyl, or (2)

and

R² is (1) hydrogen, (2) C₁₋₃alkyl, or (3) fluoro.

12. The composition of claim 11 comprising the compound wherein X is —CH=CH—, or —CH₂—CH₂; R is

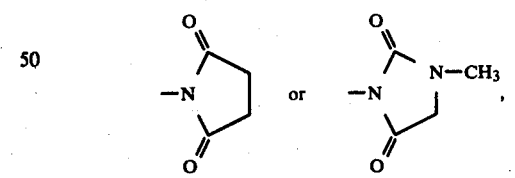

R¹ is —CH₃ and R² is hydrogen.

13. The composition of claim 12 comprising the compound wherein X is —CH=CH—; R is

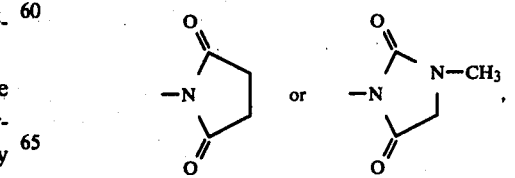

R¹ is —CH₃ and R² is hydrogen.

14. The composition of claim 13, wherein R is

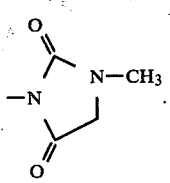

15. The composition of claim 11, 12 or 13 wherein X is —CH=CH— and Compound I is a racemate or a (—)-enantiomer.

16. A method of treating emesis, gastro-oesophageal reflux and/or dyspepsia comprising the prophylactic or therapeutic administration to a patient in need of such treatment of an effective dopamine antagonistic amount of a compound of structural formula:

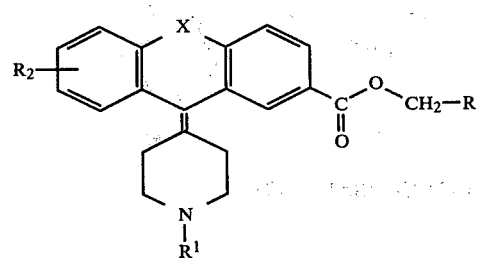

or a pharmaceutically acceptable salt thereof, wherein

X is (1) —CH=CH—, or (2) —CH$_2$—CH$_2$—;

R is

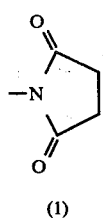 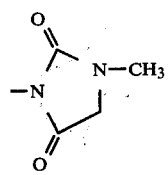

(1)  (2)

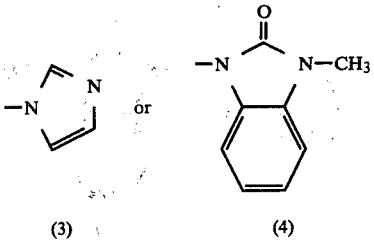

(3)  (4)

$R^1$ is (1) $C_{1-3}$alkyl, or (2)

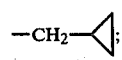

and $R^2$ is (1) hydrogen, (2) $C_{1-3}$alkyl, or (3) fluoro.

17. The method of claim 16 wherein X is —CH=CH—, or —CH$_2$—CH$_2$—; R is

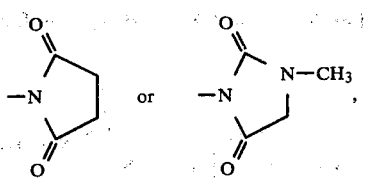

$R^1$ is —CH$_3$ and $R^2$ is hydrogen.

18. The method of claim 17 wherein X is —CH=CH—; R is

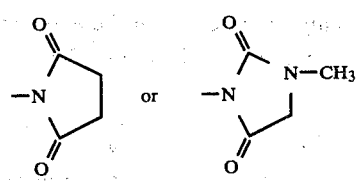

$R^1$ is —CH$_3$ and $R^2$ is hydrogen.

19. The method of claim 18, wherein R is

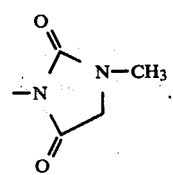

20. The method of claim 16, 17 or 18 wherein X is —CH=CH— and Compound I is a racemate or (—)-enantiomer.

* * * * *